US009078840B2

(12) United States Patent
Huo et al.

(10) Patent No.: US 9,078,840 B2
(45) Date of Patent: Jul. 14, 2015

(54) DENTAL VARNISH COMPOSITIONS

(71) Applicant: DENTSPLY International Inc., York, PA (US)

(72) Inventors: Xin Huo, Dover, DE (US); Thomas C. Simonton, Mount Wolf, PA (US)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 14/180,381

(22) Filed: Feb. 14, 2014

(65) Prior Publication Data

US 2014/0248222 A1    Sep. 4, 2014

Related U.S. Application Data

(60) Provisional application No. 61/765,062, filed on Feb. 15, 2013.

(51) Int. Cl.
*A61K 6/08* (2006.01)
*A61C 5/00* (2006.01)
*A61K 8/97* (2006.01)
*A61K 6/00* (2006.01)
*A61Q 11/00* (2006.01)

(52) U.S. Cl.
CPC .............. *A61K 8/97* (2013.01); *A61K 6/0017* (2013.01); *A61Q 11/00* (2013.01)

(58) Field of Classification Search
USPC .................................... 424/650; 523/115, 118
See application file for complete search history.

(56) References Cited

U.S. PATENT DOCUMENTS

| 3,507,822 A * | 4/1970 | Miyami ........................ 424/650 |
| 3,709,866 A * | 1/1973 | Waller ............................ 522/96 |
| 2008/0119588 A1* | 5/2008 | Orlowski et al. ............. 523/115 |
| 2008/0286212 A1 | 11/2008 | Cooley et al. |
| 2009/0324516 A1 | 12/2009 | Muscle et al. |
| 2010/0316726 A1 | 12/2010 | Prencipe et al. |

FOREIGN PATENT DOCUMENTS

| CA | 1332812 | 11/1994 |
| DE | 3634697 A1 | 4/1988 |

OTHER PUBLICATIONS

PCT International Search Report, mailed Jul. 3, 2014.
PCT Written Opinion, mailed Jul. 3, 2014.

* cited by examiner

*Primary Examiner* — Walter Webb
(74) *Attorney, Agent, or Firm* — Leana Levin; Douglas J. Hura; David A. Zdurne

(57) ABSTRACT

Disclosed herein are substantially transparent and colorless dental varnishes having improved fluoride release, transparency and color once coated.

9 Claims, 1 Drawing Sheet

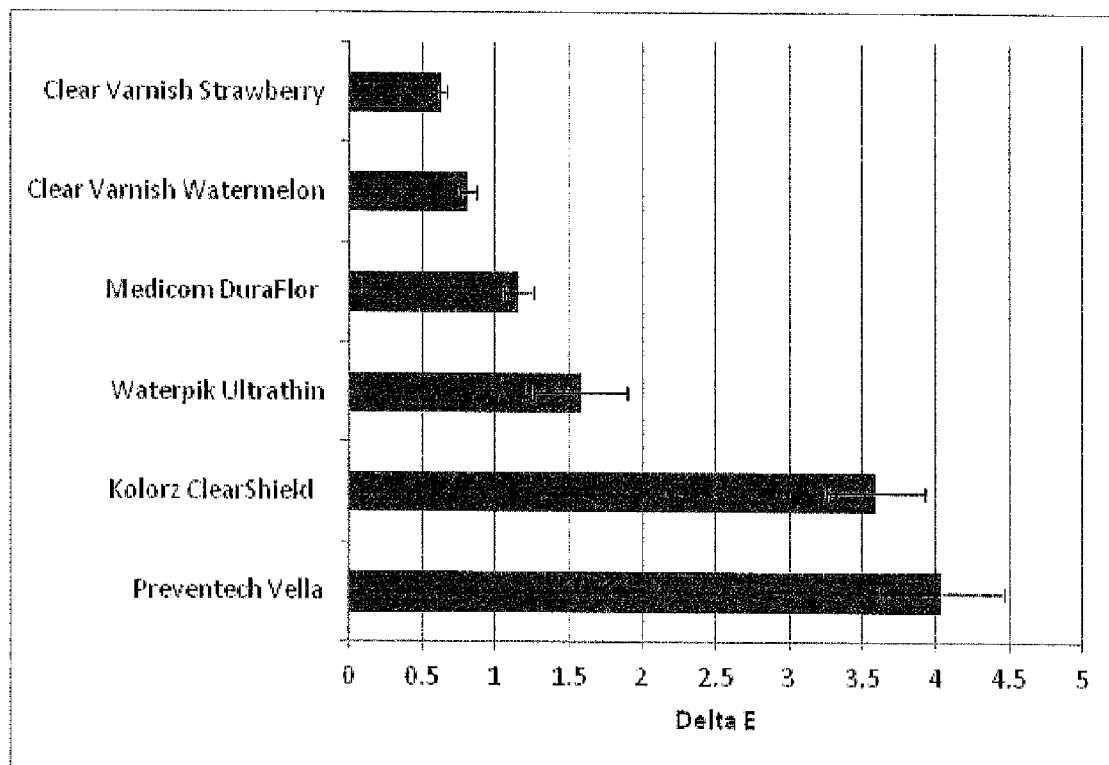

DENTAL VARNISH COMPOSITIONS

This U.S. Patent Application claims priority to U.S. Provisional Application No. 61/765,062, filed Feb. 15, 2013.

BACKGROUND

Dental varnishes known in the art are generally comprised of of natural gum rosin, sodium fluoride, and various solvents, flavor additives, sweetener and pigments. Such dental varnishes are normally applied by a brush onto a tooth surface to prevent tooth decay via a fluoride release from the composition. One of issues with the well know dental varnishes is that the fluoride release tends to be slow, i.e., more than 4 hours. This slow fluoride release results from gum rosins being use as carriers. The gum rosins used in known dental varnishes are hydrophobic and do not dissolve in saliva.

Therefore, it generally requires at least six hours of treatment time to be able to release enough fluoride ion. Another issue of traditional varnishes that most varnishes are yellow, and patients generally prefer not to draw attention to their fluoride varnished teeth. The color present in traditional varnish is caused by the dark color of natural gum rosins.

DESCRIPTION OF THE FIGURES

FIG. 1 demonstrates ΔE of varnish according to the present disclosure as compared to the ΔE of known varnishes.

SUMMARY

Described herein are dental varnishes having a rosin, resin, a fluoridizing agent, a solvent, an optional remineralization agent, an optional flavor additive, an optional sweetener and optionally an oxide. These varnishes demonstrate improved fluoride release and improved transmittance of light.

DETAILED DESCRIPTION

Disclosed herein is a dental varnish demonstrating improved fluoride release and improved transmittance of light. The dental varnish described herein is comprised of rosin, resin, a fluoridizing agent, a solvent, an optional remineralization agent, an optional flavor additive, an optional sweetener and optionally an oxide.

Rosin

In embodiments, rosins suitable for use herein include FORAL AX-E (hydrogenated gum rosin; acid number (AN) 165), STAYBELITE Resin-E (partially hydrogenated gum rosin; AN 162), PAMITE 79 (tall oil rosin; AN 164), PAMITE 79-1 (tall oil rosin; AN 158), PAMITE 90 (tall oil rosin; AN 175), POLY-PALE (partially dimerized rosin; AN 142), DYMEREX (dimerized rosin; AN 140), POLYSTIX 90 (partially dimerized rosin; AN 150), DRESINATE (rosin soap), and PERMALYN NC-11 (noncrystalline rosin; AN 157), all of which are available from Eastman Chemical Company.

Further examples of rosins suitable for use herein may be any of the commercially available types of rosin such as wood rosin, gum rosin, tall oil rosin, and mixtures thereof in their crude or refined state. The methyl ester of hydrogenated rosin, the triethylene glycol ester of hydrogenated rosin, the diethylene glycol ester of hydrogenated rosin, the ethylene glycol ester of hydrogenated rosin, and mixtures thereof with each other or with the glycerol ester of hydrogenated (partially or substantially completely) rosin are also suitable for use herein.

The rosin suitable for use herein is at least a partially hydrogenated rosin, such as a fully hydrogenated rosin. The more hydrogenated that a rosin, the more colorless it will appear to the human eye. This is because the double bonds found in rosins tend to absorb color, thus appear to have a color to the human eye. However, when the rosins are hydrogenated, less color will be absorbed thus appearing to be colorless. The rosin is necessary to the dental varnish described herein because the rosin provides the adhesion of the varnish to the tooth of a patient. Without the rosin, a dental varnish would not stick to or adhere to the teeth upon application of the varnish.

The rosin may be present in the dental varnish in amounts of from about 5 weight percent to about 75 weight percent, such as from about 18 weight percent to about 60 weight percent or from about 29 weight percent to about 35 weight percent.

Resin

The resin suitable for use in the dental varnish described herein include vinyl type resins, such as acrylic type resins, styrene type resins and the like. Examples of such vinyl monomers are 4-methacryloxyethyl trimellitic acid and its anhydride, bisphenol type epoxy acrylates and their oligomers, urethane dimethacrylates, methyl acrylate, methyl methacrylate, ethyl methacrylate, butyl methacrylate, polyethyleneglycol dimethacrylates, 2,2-bis(p-2'-hydroxy-3'-methacryloxy propoxyphenyl) propane, 2,2-bis(4-methacryloxy polyethoxy phenyl) propane, acrylonitril, vinyl acetate, 2-cyano acrylic acid esters, styrene and divinyl benzene. These vinyl monomers can be employed alone or in any mixture thereof.

The resin may be present in the dental varnish in amounts of from about 20 weight percent to about 75 weight percent, such as from about 25 weight percent to about 60 weight percent or from about 35 weight percent to about 45 weight percent.

In one embodiment, the resin may be synthesized by a reaction between 2,2' bis[p-(2'-hyroxy-3' methacry oxypropoxy)phenyl]propane (BisGMA) (about 75-95 wt. %) and hexamethylene diisocyanate (HMDI) (about 5-25 wt. %) at a temperature of from about 40° C. to about 60° C. for from about 6 to about 8 hours in a mixer at a mixing speed of from about 10 rpm to about 35 rpm. Dabco T-9 (about 0.01-0.1 wt. %) may be used as a catalyst and butylated hydroxy toluene (BHT) (about 0.01 to 0.1 wt. %) may be used as a stabilizer. This synthesized resin is especially useful as it is a substantially colorless resin. This synthesized resin in combination with a hydrogenated rosin provides for a colorless dental varnish as both the resin and the rosin are substantially colorless. As one of ordinary skill in the art will understand, any resin that is substantially colorless is suitable for use in the dental varnish described herein.

Fluoridizing Agent

In embodiments, fluoridizing agents suitable for use in the dental varnish described herein include sodium fluoride, stannous fluoride, sodium monofluorophosphate, zinc hexafluorosilicate, and sodium hexafluorosilicate. The fluoridizing agent may be present in the dental varnish in amounts of from about 0.1 weight percent to about 8 weight percent, such as from about 1 weight percent to about 7.5 weight percent or from about 2 weight percent to about 7 weight percent.

Solvent

Solvents suitable for use in the dental varnish described herein include one or more alcohols, one or more hydrocarbons or combinations therein. In some embodiments, the solvent comprises a mixture of alcohol and hydrocarbons at azeotropic or near azeotropic proportions. The relative weights given above relate only to azeotropic mixtures, and are not intended to restrict the absolute or relative amounts of alcohol and/or hydrocarbon in the dental varnish formulations. Dental varnish formulations may include individual solvents (e.g. ethyl alcohol only), or mixtures of alcohols, individual hydrocarbons or their mixtures, or mixtures of alcohols with hydrocarbons.

Alcohols suitable for use in the dental varnish described herein include $C_2$-$C_4$ alcohols, including $C_3$ alcohols, wherein said alcohols may be linear, branched and/or cyclic. Alcohols include ethyl alcohol, propyl alcohol (including its isomers n-propyl alcohol and isopropyl alcohol), butyl alcohol (including its isomers, namely n-butyl alcohol, sec-butyl alcohol, iso-butyl alcohol, and t-butyl alcohol), and blends thereof. Use of alcohols outside the $C_2$-$C_4$ range is also contemplated. Suitable hydrocarbons include $C_5$-$C_7$ hydrocarbons, including $C_6$ hydrocarbon compounds, wherein said hydrocarbons may be linear, branched and/or cyclic, and may be alkanes and/or alkenes. A hydrocarbon component may comprise a single hydrocarbon or a blend of two or more hydrocarbons. Specific suitable hydrocarbons include isopentane, n-pentane, n-hexane, isohexanes, cyclohexene, cyclohexane, methylcyclopentane, n-heptane, methyl cyclohexane, 2,5-dimethylhexane, cyclohexene, methyl cyclohexene, 1-heptene, and mixtures thereof. Use of hydrocarbons outside the $C_5$-$C_7$ range is also contemplated.

The solvent may be present in the dental varnish in amounts of from about 10 weight percent to about 35 weight percent, such as from about 15 weight percent to about 30 weight percent or from about 20 weight percent to about 25 weight percent.

Oxide

In embodiments, the dental varnish disclosed herein may be clear or substantially transparent. In alternative embodiments, the dental varnish may include a white or substantially white tint. When the dental varnish has such a tint, the dental varnish will include at least one oxide of titanium, zirconium, germanium, tin, zinc, iron, chromium, vanadium, tantalum, niobium, and mixtures thereof. When present the oxide may be present in the dental varnish in amounts of from about 0 weight percent to about 2 weight percent, such as from about 0.01 weight percent to about 1 weight percent or from about 0.08 weight percent to about 1 weight percent.

Flavor Additive and Sweetener

The dental varnish disclosed herein may include sweeteners, such as xylitol, sorbitol, sucralose, aspartame, sodium saccharin, and mixtures thereof. Such sweeteners may be in the dental varnish in amounts of from about 0.01 weight percent to about 2 weight percent, such as from about 0.05 weight percent to about 1.5 weight percent or from about 0.08 weight percent to about 1 weight percent.

The dental varnish disclosed herein may include flavorings, including but not limited to, peppermint, watermelon, wintergreen, spearmint, cherry, citric acid, orange, strawberry, vanilla, coconut, bubble gum flavors and mixtures thereof. Such flavoring additives may be in the dental varnish in amounts of from about 0.01 weight percent to about 5 weight percent, such as from about 0.1 weight percent to about 4 weight percent or from about 0.7 weight percent to about 3 weight percent.

The resulting dental varnish may have a transparent or white color, or a substantially transparent color having a white or off-white tine. The viscosity of the dental varnish may be from about 500 cp to about 10,000 cp at 25° C. The specific gravity of the dental varnish may be from about 1 to about 1.2 g/cm³. Unlike prior art dental varnishes, the dental varnish disclosed herein is capable of being transparent or substantially transparent, has a high fluoride release within the first two hours of application, and is capable of being smoothly coated onto a patient's tooth.

Suitable precursor resins include, for example, 2,2' bis[p-(2'-hyroxy-3' methacry oxypropoxy)phenyl]propane (Bis-GMA), and the like. A resin suitable for use in the dental varnish disclosed herein includes and ethoxylated (2) bisphenol A dimethacrylate:

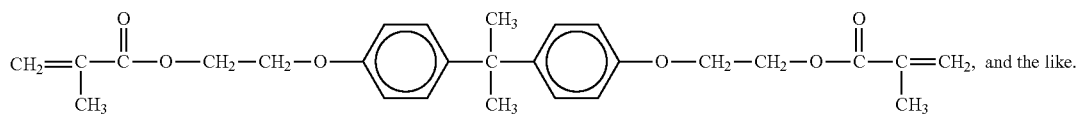

and the like.

The varnish resin may be made by reacting a suitable precursor resin with an isocyanate, such as, hexamethylene diisocyanate (HMDI) at a temperature of from about 40° C. to about 60° C. for a time period of from about 6 hours to about 8 hours in a Ross or Premier mixer at a mixing speed of from about 12 rpm to about 25 rpm. Stannous type cataylsts, such as Dabco T-9 (stannous octoate), and at least one stabilizer are suitable for use in manufacturing the dental varnish disclosed herein.

Stabilizers suitable for use in preparing the dental varnish include butylated hydroxyanisole (BHA), butylated hydroxytoluene (butylhydroxytoluene, BHT), propyl gallate (propyl 3,4,5-trihydroxybenzoate), tert-butylhydroquinone (TBHQ, tertiary butylhydroquinone), calcium propanoate (or calcium propionate), from liquid phenolic compounds such as mixed tocopherols (tocopherols, Vitamin E), rosemary extract, the liquid phenolic acid oregano oil (origanum oil), vegetable oil, from the quinoline-based antioxidant liquid ethoxyquin, from the acid-based antioxidant calcium propanoate (or calcium propionate), and from derivatives or mixtures thereof.

The dental varnishes disclosed herein exhibit improved fluoride release over 2 hour, 4 hour and 6 hour time periods. At 2 hours, the dental varnishes described herein exhibit a fluoride release of about 14000 µg/g to about 17000 µg/g, such as from about 14500 µg/g to about 16500 µg/g or about 15000 µg/g to about 16000 µg/g. At 4 hours, the dental varnishes described herein exhibit a fluoride release of about 2000 µg/g to about 6000 µg/g, such as from about 2750 µg/g to about 5500 µg/g or from about 3250 µg/g to about 4250 µg/g. At 6 hours, the dental varnishes described herein exhibit a fluoride release of about 1000 µg/g to about 5000 µg/g, such as from about 1250 µg/g to about 3500 µg/g or from about 2000 µg/g to about 3000 µg/g. This amount of fluoride release is a significant improvement over known, competitive dental varnishes.

The dental varnishes disclosed herein exhibit improved ΔE, which refers to color change between two colors, in this case the color change between the shade of a tooth having a dental varnish thereon and a tooth having no dental varnish. In other words, the dental varnishes according to the present disclosure are colorless. A ΔE of less than 1 is not capable of being noticed or perceived by the human eye. The dental varnishes according to the present disclosure have a ΔE of less than 1, such as from about 0.05 to about 0.98 or from about 0.1 to about 0.9 or from about 0.2 to about 0.85. Such a ΔE is a statistical improvement over known dental varnishes.

In addition to being colorless, the dental varnishes disclosed herein are also transparent. Transparency is evaluated by the transmittance (%). The higher the transmittance percentage, the more transparent is a dental varnish. The transparency of the dental varnish described herein is at least 50%, such as from about 55% to about 95%, such as from about 60% to about 85% or from about 60% to about 80%. These transmittance percentages or transparencies are significant improvements over known, competitive dental varnishes.

The dental varnishes described herein may be applied to teeth using a suitable applicator, such as a brush, as is well understood by those skilled in the art. Methods of using the dental varnish to seal a tooth include applying the dental varnish to a tooth.

Test Results

Fluoride Release

A varnish sample weighing from about 0.02 g to 0.05 g was applied on the bottom of a ¼ oz white polypropylene cup. 25 ml of deionized water was then added into the cup and pulled out after 2 hours of soaking. Fluoride ion released into the deionized water was measured by an ion selective electrode. Fresh deionized water was then added into the cup and the same procedure was repeated to measure fluoride release after 4 hrs and 6 hrs.

Table 1 demonstrates a comparison of fluoride release between two clear varnishes with different flavor and competitors' varnish product. It was found in Table 1 that the two clear varnishes according to the present disclosure released significantly more fluoride than the competitors' varnish did in first two hours.

In addition, the two clear varnishes continued to release more fluoride than the competitors' varnish over 4 hours (see Table 1). The clear varnish according the present disclosure also released more fluoride than Preventech Vella, Waterpik Ultrathin, Medicom DuraFlor and Kolorz Clearshield over 6 hours.

TABLE 1

Comparison of fluoride release between two Clear Varnishes with different flavors and competitors' product.

| | Fluoride Release (μg/g) | | |
|---|---|---|---|
| Sample # | 2 hours | 4 hours | 6 hours |
| Clear Varnish Watermelon Lot#120815-1 | 15434 ± 750 | 3663 ± 630 | 1647 ± 242 |
| Clear Varnish Strawberry Lot#120815 | 15345 ± 1980 | 3938 ± 405 | 2399 ± 263 |
| Preventech Vella Lot#38227 | 6319 ± 409 | 1178 ± 135 | 772 ± 76 |
| VoCo Profluorid Lot#1201189 | 6184 ± 399 | 2038 ± 59 | 1364 ± 24 |
| Waterpik Ultrathin Lot#37500 | 5295 ± 1221 | 945 ± 239 | 674 ± 160 |
| Medicom DuraFlor Lot#39924 | 5072 ± 1116 | 925 ± 131 | 610 ± 71 |
| Kolorz ClearShield Lot#38651 | 4797 ± 873 | 922 ± 193 | 646 ± 124 |

The clear varnishes of Table 1 were prepared by first mixing about 285 grams of 2-propanol with:
(1) about 520 grams of resin, derived from 2,2' bis[p-(2'hydroxy-3'methacryl(oxypropoxy)phenyl]propane (BisGMA), hexamethylene diisocyanate (HDMI), butylated hydroxyl toluene (BHT) and T-9 catalyst, and
(2) about 400 grams of fully hydrogenated rosin.

These components were mixed for from about 2 hours to about 14 hours until all of the resin and rosin was dissolved thereby creating a solution. About 65 grams of sodium fluoride, about 1.5 grams of sweetener and 20 grams of flavoring added and the resulting solution was mixed from about 1 hour to about 2 hours until a uniform suspension was formed.

The resin described above was synthesized by charging a mixture of about 1000 grams of BisGMA, about 171 grams of HDMI, about 0.57 grams of BHT and about 0.57 grams of T-9 into a Ross mixer (Model LDM-1, Charles Ross and Son Co.) equipped with a water jacket and two agitators. The water jacket temperature was increase to 50° C. The mixture was agitated for about 7 hours.

The two Clear Varnishes having watermelon and strawberry flavoring released more fluoride in the first two hours than major competitors and continued to release more fluoride over the 4 and 6 hour time periods.

Color Test

Four composite chips (n=4) were prepared using Dentsply Universal Composite, EsthetX HD A2 shade. Composite was filled into a stainless steel ring mold with a dimension of 30 mm (inside diameter)×1.0 mm (thickness) and covered with a pair of glass plates on the top and bottom of composite. The composite was then cured with a Triad 2000 curing light (Dentsply) for about 2 minutes on each side. Color value: $L^*$, $a^*$, and $b^*$ of the prepared chips were measured using Color i5, a colorimeter manufactured by Gretagmacbeth. A dental varnish sample was mixed using a varnish brush until an uniform slurry was formed. About 0.06 gram of varnish was weighed and spread on the top of each of the composite chips to make a uniform coating using a varnish brush. The coating was dried at room temperature for at least 24 hours until the coating was completely dry. $L^*$, $a^*$, and $b^*$ value of the coated surface was measured by the colorimeter.

ΔE was calculated using the following formula:

$$\Delta E = ((a_1^* - a_2^*)^2 + (b_1^* - b_2^*)^2 + (L_1^* - L_2^*)^2)^{1/2}$$

$a_1^*$: Red & Green value before varnish coating
$a_2^*$: Red & Green value after varnish coating
$b_1^*$: Yellow & Blue value before varnish coating
$b_2^*$: Yellow & Blue value after varnish coating
$L_1^*$: Lightness value before varnish coating
$L_2^*$: Lightness value after varnish coating Table 2 shows a comparison of color change between two clear varnishes with different flavor according to the present disclosure and competitors' varnish products. The color change before and after coating was measured by the value of ΔE, which is defined as the difference between two colors in an $L^*a^*b^*$ color space. It is universally valid that when ΔE is less than 2, the color difference will not be perceived by human eyes. As demonstrated in Table 2 below, ΔE of the two Clear Varnishes according to the present disclosure was less than 2. Therefore, the two clear coatings did not change the shade of the teeth or alter the color of teeth.

In addition, Table 2 also demonstrates that the ΔE of two clear varnishes was statistically lower than Kolorz ClearShield, Waterpik Ultrathin and Preventech Vella and were comparable to Medicom DuraFlor.

TABLE 2

Comparison of Delta E between two Clear Varnishes with different flavor and competitors' product.

| | Delta E | |
|---|---|---|
| Sample # | Average | Standard Deviation |
| Clear Varnish Strawberry Lot#120815 | 0.63 | 0.04 |
| Clear Varnish Watermelon Lot#120815-1 | 0.81 | 0.06 |
| Medicom DuraFlor Lot#39924 | 1.16 | 0.10 |
| Waterpik Ultrathin Lot#37500 | 1.58 | 0.32 |
| Kolorz ClearShield Lot#38651 | 3.59 | 0.34 |
| Preventech Vella Lot#38227 | 4.04 | 0.42 |

As demonstrated in FIG. 1, the ΔE of the two Clear Varnishes according to the present disclosure has met the stated acceptance criteria and are considered colorless on a tooth surface. The ΔE of the two clear varnishes according to the present disclosure was statistically lower than Kolorz ClearShield, Waterpik Ultrathin and Preventech Vella and is comparable to Medicom DuraFlor.

Transparency Test

From about 0.08 to 0.12 grams of dental varnish was weighed on a mylar sheet, and the sample was arranged into a rectangular shape (about 10 mm×5 mm) using a stainless steel spatula. The 2 mil side of a Wet Film Applicator was used and drawn down against the varnish at a constant speed of about one inch per second. A minimum of nine specimens (n=9) was needed for each varnish product. The transmittance of the drawn-down varnish was measured by a UV-vis spectrophotometer.

Table 3 shows a comparison of the transmittance between two clear varnishes with different flavor according to the present disclosure and competitors' varnish products. The transmittance is the fraction of incident light at a specified wavelength that passes through a sample. The higher the transmittance, the more transparent the sample is. As demonstrated in Table 3, the transmittance of the two Clear Varnishes with different flavor according to the present disclosure was statistically higher than their competitors' varnish.

TABLE 3

Comparison of Transmittance between two Clear Varnishes with different flavor and competitors' product.

| | Transmittance (%) | |
|---|---|---|
| Sample # | Average | Standard Deviation |
| Clear Varnish Strawberry Lot#120815 | 65.6 | 3.5 |
| Clear Varnish Watermelon Lot#120815-1 | 65.1 | 1.9 |
| VoCo Profluorid Lot#1201189 | 48.9 | 4.9 |
| Kolorz ClearShield Lot#38651 | 35.3 | 2.1 |
| Medicom DuraFlor Lot#39924 | 34.9 | 3.1 |
| Waterpik Ultrathin Lot#37500 | 26.1 | 2.8 |

As can be seen from Table 3, the Clear with Strawberry and Watermelon flavor according to the present disclosure were more transparent than any of the competitors' varnish products.

It will be appreciated that various of the above-disclosed compositions and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

We claim:

1. A dental varnish comprising a rosin, resin, a fluoridizing agent, a solvent, an optional remineralization agent, an optional flavor additive, an optional sweetener and optionally an oxide, wherein the dental varnish is transparent, exhibiting a transmittance of at least 50%, wherein the rosin is present in the dental varnish from about 18 to about 60 percent by weight and wherein the resin is a reaction product of 2,2' bis[p-(2'-hydroxy-3' methacryloxypropoxy)phenyl]propane (BisGMA) and hexamethylene diisocyanate (HMDI) and is present in the dental varnish from about 25 to about 60 percent by weight.

2. The dental varnish according to claim 1, wherein the rosin is a hydrogenated rosin.

3. The dental varnish according to claim 2, wherein the rosin is at least a partially hydrogenated rosin.

4. The dental varnish according to claim 1, wherein the dental varnish exhibits a fluoride release over a two hour time period of from 14000 μg/g to 17000 μg/g.

5. The dental varnish according to claim 1, wherein the dental varnish exhibits a ΔE of less than 1.

6. The dental varnish according to claim 5, wherein the ΔE is from 0.05 to 0.98.

7. The dental varnish according to claim 1, wherein the transmittance is from 55% to 95%.

8. The dental varnish according to claim 1, wherein the rosin is present in the dental varnish in amounts of from 29 weight percent to 35 weight percent.

9. The dental varnish according to claim 1 comprising the remineralization agent.

* * * * *